United States Patent [19]

Moss

[11] Patent Number: 5,798,392
[45] Date of Patent: Aug. 25, 1998

[54] SULFONYL FLUORIDES FOR THE TREATMENT OF ALZHEIMER'S DISEASE

[75] Inventor: Donald Eugene Moss, El Paso, Tex.

[73] Assignee: The Board of Regents of the University of Texas System, Austin, Tex.

[21] Appl. No.: 705,858

[22] Filed: Aug. 28, 1996

[51] Int. Cl.$^6$ .......................... A61K 31/135; A61K 31/10
[52] U.S. Cl. ............................................. 514/649; 514/709
[58] Field of Search ....................................... 514/649, 709

[56] References Cited

PUBLICATIONS

CA 118: 183249, Palacios–Esquivel et al., 1993.
CA 110: 147634, Moss et al., 1988.
CA 106: 188458, Moss et al., 1986.

*Primary Examiner*—Kimberly Jordan
*Attorney, Agent, or Firm*—Benjamin Aaron Adler

[57] ABSTRACT

The present invention provides a pharmaceutical composition, comprising a sulfonyl fluoride and a pharmaceutically acceptable carrier. Also provided is a method of treating Alzheimer's disease in an individual in need of such treatment, comprising the step of administering to said individual a therapeutically effective dose of methanesulfonyl fluoride. Further provided is a method of enhancing cognitive performance in an individual in need of such treatment, comprising the step of administering to said individual a therapeutically effective dose of methanesulfonyl fluoride.

13 Claims, 9 Drawing Sheets

SULFONYL FLUORIDES FOR THE TREATMENT OF ALZHEIMER'S DISEASE

BACKGROUND OF THE INVENTION

1. Field of the Invention

The present invention relates generally to the fields of neurology and the pharmacotherapy of Alzheimer's Disease. More specifically, the present invention relates to the novel use of sulfonyl fluorides for the treatment of Alzheimer's Disease.

2. Description of the Related Art

Neuropathological evidence demonstrating an extensive loss of cholinergic function in the basal forebrain and cortex in senile dementia of the Alzheimer type (SDAT) has been confirmed by many investigators and is a relatively common feature of the disease [1,2,3]. The reduction in cholinergic function may, at least in part, be responsible for cognitive decline in this disease [4,5]. One treatment strategy that has attracted considerable attention is the use of cholinesterase (ChE) inhibitors to increase the concentration of acetylcholine in the brain, thereby increasing cholinergic function and improving cognitive performance [4,6,7,8].

The problem, however, has been to develop an effective, relatively nontoxic inhibitor for acetylcholinesterase (acetylcholinesterase , EC 3.1.1.7), the enzyme widely accepted as involved in memory functions [5,9]. Cholinesterase inhibitors, in general, are a relatively toxic compounds because significant inhibition of these enzymes in peripheral tissues are associated with nausea, vomiting, diarrhea, excessive salivation, and other signs of excessive cholinergic activity. In addition, there is some evidence that inhibition of butyrylcholinesterase (BChE, E.C. 3.1.1.8), concurrently with acetylcholinesterase (AChE, E.C. 3.1.1.7), potentiates the toxicity of cholinesterase inhibitors in peripheral smooth muscle [10]. The ideal cholinesterase inhibitor to be used for the treatment of a chronic disease such as SDAT would, therefore, be selective for the CNS (compared to peripheral tissues), be long acting, and have a high degree of selectivity for acetylcholinesterase (compared to butyrylcholinesterase).

Methanesulfonyl fluoride (MSF) is a long-acting irreversible inhibitor of acetylcholinesterase that shows excellent selectivity for the CNS [11,12]. This selectivity seems to be due, in part, to the irreversible mechanism of action. Recovery from irreversible inhibition is a simple function of the rate of new synthesis of acetylcholinesterase in each tissue. Fortunately, acetylcholinesterase in the brain is resynthesized at a rate much slower than peripheral tissues [11,12]. Therefore, methanesulfonyl fluoride can be used to accumulate up to 80–90% inhibition of rodent and monkey brain acetylcholinesterase with minimum inhibition of peripheral enzyme and without toxicity by using relatively small doses of the drug over a long period of time [11,12].

Methanesulfonyl fluoride also has high selectivity as an inhibitor of acetylcholinesterase in comparison to butyrylcholinesterase and is much better with regard to this quality than tacrine, metrifonate, and physostigmine which do not show this high degree of selectivity [13]. This may also be one mechanism by which methanesulfonyl fluoride avoids peripheral toxicity. In summary, therefore, methanesulfonyl fluoride is a long-acting, acetylcholinesterase-selective inhibitor that can produce up to 80–90% inhibition in the brain without toxicity.

Despite the research discussed supra, there are significant problems in this art in determining whether a potential therapeutic pharmaceutical will be clinically efficacious in humans. For example, Schwarz et al. reviewed the use of cholinesterase inhibitors for the treatment of Alzheimer's disease and concluded that irreversible inhibitors, specifically including methanesulfonyl fluoride, were too dangerous and toxic and that physicians are more confortable with reversible drugs. Adem (1993) while reviewing the "next generation of cholinesterase inhibitors" omitted discussing the sulfonyl fluorides while focusing on noncholinesterase inhibiting effects.

The prior art is deficient in the lack of effective and improved means of treating individuals with Alzheimer's Disease. The present invention fulfills this longstanding need and desire in the art.

SUMMARY OF THE INVENTION

The novel treatment strategy with an irreversible acetylcholinesterase inhibitor is based on the brain recovering from inhibition (resynthesizing the enzyme) more slowly than peripheral tissues. Using this special quality of brain tissue, small doses of methanesulfonyl fluoride administered over time can accumulate very high levels of inhibition in the brain without toxic cholinergic effects in peripheral tissues. The peripheral tissues are protected because they resynthesize the enzyme relatively quickly [11,12]. Using this strategy, therefore, it was expected that methanesulfonyl fluoride could produce more than 50% inhibition in the brain, the minimum therapeutic window [7,14,15], without toxic effects in peripheral tissues. A minimum of 50% inhibition also corresponds to strong methanesulfonyl fluoride-induced enhancement of animal memory without toxicity [16,17,18].

In one embodiment of the present invention, there is provided a composition of matter comprising a pharmaceutical composition, comprising a sulfonyl fluoride and a pharmaceutically acceptable carrier.

In another embodiment of the present invention, there is provided a method of treating Alzheimer's disease in an individual in need of such treatment, comprising the step of administering to said individual a therapeutically effective dose of a sulfonyl fluoride.

In yet another embodiment of the present invention, there is provided a method of enhancing cognitive performance in an individual in need of such treatment, comprising the step of administering to said individual a therapeutically effective dose of a sulfonyl fluoride.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
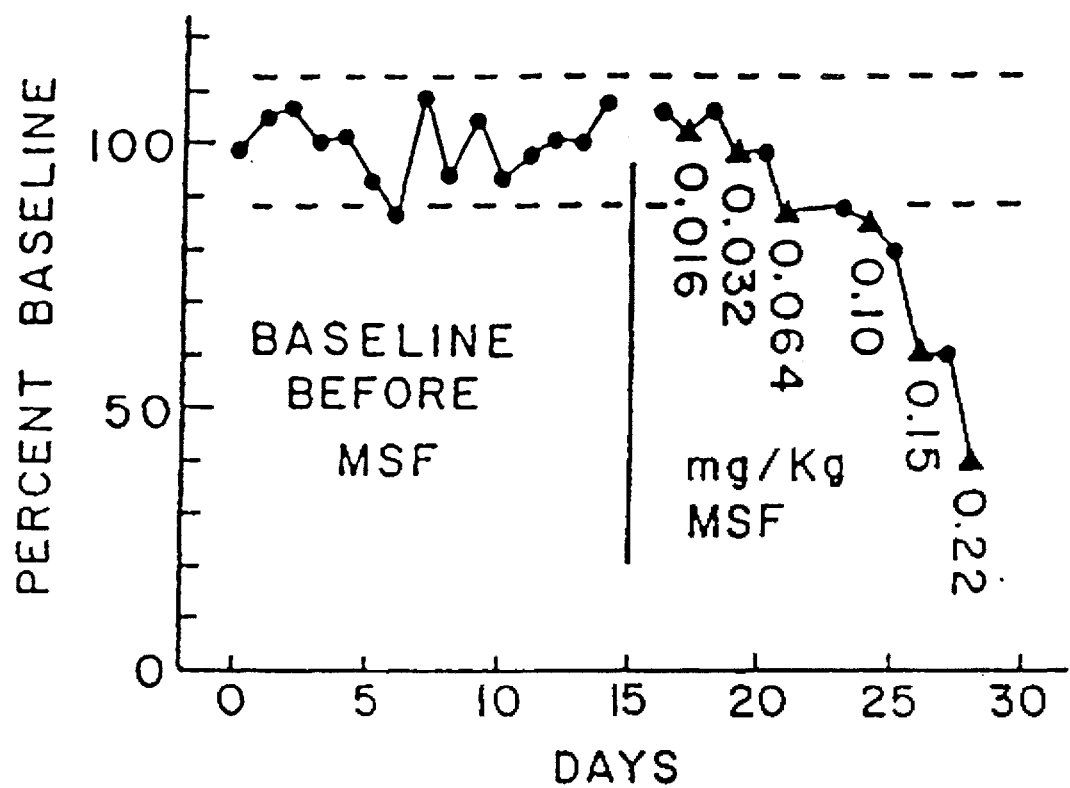
FIG. 1 shows the effects of methanesulfonyl fluoride (mg/kg) on erythrocyte acetylcholinesterase.

The present invention is directed to a pharmaceutical composition, comprising a sulfonyl fluoride and a pharmaceutically acceptable carrier. Representative examples of sulfonyl fluorides include methanesulfonyl fluoride, phenylmethanesulfonyl fluoride, 3-amino-4-methylbenzenesulfonyl fluoride, 4-methoxymetanilyl fluoride, and ethanesulfonyl fluoride, benzenesulfonyl fluoride, para-toluenesulfonyl fluoride, 3-amino-4-ethoxybenzenesulfonyl fluoride, 3-amino-4-chlorobenzenesulfonyl fluoride, and isopropylsulfonyl fluoride.

Preferably, the sulfonly fluoride, such as methanesulfonyl fluoride is contained in said composition in an amount of from about 20 mg/ml to about 100 mg/ml. This concentration of methanesulfonyl fluoride makes a volume that can be included in a capsule and is within the limits of solubility of methanesulfonyl fluoride in oil.

Similarly, the pharmaceutically acceptable carrier is preferably selected from the group consisting of any USP/NF approved vegetable oil consisting of peanut oil, sesame oil, sunflower seed oil, wheat germ oil, or synthetic oils. The reason for using oils is the chemical stability of MSF which would degrade in water solutions. Experiments in rats and monkeys show that methanesulfonyl fluoride will be pharmacologically active if injected intramuscularly in a similar sterile oil vehicle. The route of administration may be other than oral.

Other therapeutic compounds may optionally be administered either concurrently with methanesulfonyl fluoride or otherwise, e.g., in a coordinated drug regimen to enhance the therapeutic effects of methanesulfonyl fluoride. Such compounds are short acting and require administration 2 or 3 times per day. It may be pharmacokinetically better to give such compounds less often. Representative compounds include:

(1) RS86 (2-ethyl-8-methyl-2,8-diazospiro-4,5-decan-1, 3-dion-hydrobromide), a long-acting and specific muscarinic agonist. This compound (and other muscarinic agonists) is expected to enhance cholinergic activity in Alzheimer's disease by direct stimulation of muscarinic acetylcholine receptors and has been suggested as a therapeutic agent (Davidson, M., Hollander, E., Zemishlany, Z., Cohen, L. J., Mohs, R. C., and Davis, K. L. Cholinergic agonists in Alzheimer's disease patients. In: *Current Research in Alzheimer Therapy*, E. Giacobini and R. Becker (Eds.), New York, Taylor and Francis, 1988, pp. 333–336). If RS 86 were used in coordination with methanesulfonyl fluoride, it would be contained in said composition in an amount of from about 5 mg/ml to about 25 mg/ml in the same oils as suggested for MSF. The actual dosage would be from about 0.5 mg to 1.5 mg orally (whole patient dose) three times per day (Davidson et al., 1988).

(2) 4AP (4-aminopyridine), a potassium channel blocker. This compound (and other potassium channes blockers) is expected to enhance acetylcholine release and increase synthesis of acetylcholine and has been suggested as a therapeutic agent in Alzheimer's disease (Wiseman, E. J. and Jarvik, L. F., Potassium channes blockers: could they work in Alzheimer's disease? *Alzheimer's Disease and Associated Disorders* 5: 25–30, 1991; Waser, P. G., Berger, S., Haas, H. L., and Hofman, A., 4-Aminopuridine (4-AP) -derivatives as central cholinergic agents. In: *Current Research in Alzheimer Therapy*, E. Giacobini and R. Becker (Eds.), New York, Taylor and Francis, 1988, pp. 337–342). If 4AP were used, it would be contained in said composition in an amount of from about 25 mg/ml to about 100 mg/ml in the same oils as suggested for MSF. The actual dosage would be from about 2.5 mg to about 10 mg (whole patient dose) twice a day orally (Wiseman and Jarvik, 1991).

(3) Lecithin (complex mixture containing at least 12% phosphatidylcholine as the active ingredient). Phosphatidylcholine is readily absorbed orally and is broken down into choline and provides this precursor for the synthesis of acetylcholine and prevents possible depletion of choline from membranes when stimulating cholinergic function in Alzheimer's disease (Wurtman, et al., Cholinesterase inhibitors increase the brain's need for free choline. In: *Current Research in Alzheimer Therapy*, E. Giacobini and R. Becker (Eds.), NY, Taylor and Francis, 1988, pp. 95–100). Lecithin has also actually been used in combination to enhance the effects of cholinesterase inhibitors (in this case tacrine) in the treatment of cognitive deficits in Alzheimer's disease (Gauthier, et al., Tetrahydroaminoacridine and lecithin in Alzheimer's disease. In: *Current Research in Alzheimer Therapy*, E. Giacobini and R. Becker (Eds.), New York, Taylor and Francis, 1988, pp. 237–245). Lecithin containing about 12% phosphatidylcholine would be contained in capsules of about 1 to 2 grams each and given in a total daily dose of about 5 to 10 grams per day.

The present invention is also directed to a method of treating Alzheimer's disease in an individual in need of such treatment, comprising the step of administering to said individual a therapeutically effective dose of methanesulfonyl fluoride. Preferably, the dose of methanesulfonyl fluoride is from about 0.15 mg/kg to about 0.5 mg/kg. The methanesulfonyl fluoride would generally be administered in a pharmaceutically acceptable excipient, such as those described above. In another embodiment of this method, a physician may find it desirable to combine the therapeutic effects of methanesulfonyl fluoride with a therapeutically effective dose of a compound such as RS86, 4AP, and lecithin in the doses suggested above.

There are various tests known to those having skill in this art for determining whether a pharmaceutical is therapeutically efficacious in treating Alzheimer's disease in an individual. Representative examples of such tests include the Alzheimer's Disease Assessment Scale (ADAS), the Mini-Mental State Exam (MMSE), Clinical Interview Based Impression of Change (CIBIC), and the Global Deterioration Scale.

The present invention is further directed to a method of enhancing cognitive performance in an individual in need of such treatment, comprising the step of administering to said individual a therapeutically effective dose of methanesulfonyl fluoride. Preferably, the dose of methanesulfonyl fluoride is from about 0.15 mg/kg to about 0.5 mg/kg of the recipient's body weight. The methanesulfonyl fluoride would generally be administered in a pharmaceutically acceptable excipient, such as those described above. Generally, this method of enhancing cognitive function would be useful in an individual with a with neurological disease such as Parkinson's disease, Parkinsons dementia complex of Guam, Boxer's dementia, and any other diseases or disorders characterized by insufficient acetylcholine in the central nervous system. Methanesulfonyl fluoride will be an effective treatment of "normal age-related memory impairment" which is not a disease but normal memory loss with aging. As described below, there are various tests known to those having skill in this art for determining whether a pharmaceutical enhances cognitive performance in a human. Representative examples of such tests include ADAS, MMSE, CIBIC and Global Deterioration.

Experiment I below was a pilot experiment on one person to demonstrate: 1) that methanesulfonyl fluoride is biologically active after oral administration; 2) that methanesulfonyl fluoride is not toxic to humans at doses that might have therapeutic value in treating SDAT; and 3) the dose/response data to estimate the required therapeutic dose. Experiment II was conducted on a group of 10 normal volunteers to confirm, in a larger group of subjects, the dose/response data and the absence of toxicity observed in Experiment I. Experiment III was the first test of methanesulfonyl fluoride as a therapeutic agent in fifteen patients suffering with dementia. The purpose of Experiment III was to obtain a preliminary estimate of efficacy. These experiments demonstrate that sulfonyl fluorides are novel therapeutic agents that have significant utility in the treatment of Alzheimer's disease. The present invention, besides demonstrating clear efficacy of methanesulfonyl fluoride as a therapeutic agent, also shows how to use these therapeutic agents to avoid toxicity.

The following examples are given for the purpose of illustrating various embodiments of the invention and are not meant to limit the present invention in any fashion.

EXAMPLE 1

Experiment I

The first normal volunteer to receive methanesulfonyl fluoride was a 50 year old male weighing 90 kg. Informed consent was obtained and baseline clinical blood values were normal.

The methanesulfonyl fluoride used in these experiments was custom synthesized by MTM Chemical Co. (Blythewood, S.C., now a part of Lancaster Synthesis) specifically to meet the FDA requirements for identity, purity, and strength and these qualities were documented by independent testing. The methanesulfonyl fluoride was made into an oral formulation by dilution into peanut oil (U.S.P./N.F., Spectrum Chemical Mfg. Corp., Gardena, Calif.) to make a dose that could be contained in a Number 2 gelatin capsule (Eli Lilly and Co., Indianapolis, Ind.). Organophosphates such as di-isopropyl fluorophosphate, which are generally more reactive than sulfonyl fluorides, are stable in peanut oil more than one year [19].

Erythrocyte acetylcholinesterase (AChE) and plasma butyrylcholinesterase (BChE) were assayed according to the spectrophotometric method of Ellman et al., *Biochem. Pharmacol.* 7, 88–95, 1961, except at pH 7.4, using acetyl-β-methylthiocholine and butyrylthiocholine substrates, respectively. These procedures, described below, allowed rapid determination of cholinesterase levels from a drop of blood drawn by finger prick.

EXAMPLE 2

Cholinesterase Assays

The effect of methanesulfonyl fluoride was determined by measuring the inhibition of erythrocyte acetylcholinesterase or plasma butyrylcholinesterase. Blood was drawn by finger prick into Micro-Cal (Chase Instruments, Glens Falls, N.Y.) heparinized hematocrit capillary tubes. Cholinesterase activity was determined by the procedure of Ellman, et al., except at pH 7.4. Substrates were made in deionized water (acetyl-β-methylthiocholine and butyrylthiocholine; Sigma Chemical Co., St. Louis, Mo.) and the assays were run in triplicate at 25° C. The 3.0 ml assay medium contained 2.8 ml of 0.1M (Na) phosphate buffer (pH 7.4), 0.1 ml Ellman's reagent (0M 5,5'dithio-bis-2-nitrobenzoic acid, Sigma Chemical Co., St. Louis, Mo.), and the negligible volume of the enzyme. The reactions were started by the addition of 0.1 ml substrate. Absorbance differences (initially zero) were followed at 412 nm. The reactions were linear for more than 20 minutes.

EXAMPLE 3

Plasma Butyrylcholinesterase

Three filled hematocrit tubes were plugged and centrifuged at 1000×g for 5 minutes and the plasma was assayed separately by scoring and breaking the tubes at the interface between the red cells and plasma. The portion of each of 3 capillary tubes containing plasma were weighed, the contents were blown out into a waiting cuvette, and the empty tube was weighed again to determine by subtraction the amount of plasma added to each of three cuvettes. The plasma butyrylcholinesterase was then assayed using butyrylthiocholine substrate. The Michaelis constant ($K_m$) was 190.9 μM (SEM 11.7 μM) for butyrylthiocholine substrate under these conditions. Butyrylcholinesterase $V_{max}$ was 4.853 (SEM=0.135)×$10^{-6}$ moles/min/gm plasma.

EXAMPLE 4

Erythrocyte Acetylcholinesterase

The erythrocyte acetylcholinesterase assays were conducted in a different manner because the packed erythrocytes remaining in the capillary tubes contained residual plasma and the cells were clumped and unsatisfactory for enzyme assays. Therefore, erythrocyte acetylcholinesterase activity was determined by first diluting whole blood (erythrocytes and plasma) contained in one capillary tube into a total of 20 ml of 0.1M (Na) $PO_4$ buffer, pH 7.4. The amount of blood added was measured by weighing the full capillary tube before adding the contents into the buffer and then subtracting the empty weight of the tube. The blood was mixed thoroughly in the buffer and then 2.8 ml of the blood/buffer mixture and 0.1 ml of Ellman's reagent were added to each of 6 identical tubes with magnetic stirring.

The combined total enzyme activity of erythrocyte acetylcholinesterase and plasma butyrylcholinesterase against acetyl-β-methylthiocholine was determined by adding 0.1 ml of substrate solution to three of the tubes for 5 minutes. At the end of 5 minutes, substrate was added to the other three tubes. The stir bars were quickly removed and all six tubes were centrifuged at 1000×g for 5 minutes to remove the erythrocytes. The supernatant was placed in 3 pairs of matched cuvettes and the absorbance difference was recorded and the cuvettes were quickly replaced in the holder at 25° with stirring for 5 more minutes.

At the time of the first spectrophotometric reading of the supernatants, the only difference between the three pairs of supernatant samples was that one of each pair had substrate 5 minutes longer than the other. The difference between the absorbance of the cuvettes in each pair was, therefore, a measure of enzyme activity for whole blood (both erythrocyte acetylcholinesterase and plasma butyrylcholinesterase) for 5 minutes.

Exactly 5 minutes after the absorbance of the cuvettes had been first recorded to measure the effects of whole blood, the absorbance was recorded again. The difference between the absorbance first recorded for each cuvette and the second absorbance recorded 5 minutes later was a measure of the activity of plasma butyrylcholinesterase included in the whole blood. Although acetyl-β-methylthiocholine is not a good substrate for plasma butyrylcholinesterase, it was important to correct for this activity to obtain the best estimate of erythrocyte acetylcholinesterase activity. Therefore, the activity of the erythrocyte acetylcholinesterase (which had been removed when the erythrocytes were centrifuged out) was calculated by subtracting the activity of plasma butyrylcholinesterase from the activity of whole blood. Erythrocyte acetylcholinesterase activity was finally expressed relative to grams of erythrocytes (percent of whole blood weight) estimated from the hematocrit for each patient and the weight of whole blood added to each sample at the beginning of the assay. On average, the assay could be conducted with about 13–15 mg whole blood, the capacity of one micro-capillary tube.

The assay was linear for more than 20 minutes. The erythrocyte acetylcholinesterase assay procedure required only about 15 minutes per sample and gave reliable results. Experiments indicated that this procedure produces results equivalent to washing erythrocytes in buffer and resuspending them for assays. This capillary procedure had the advantage of being much faster and it gave reliable results from a very small sample that did not require venipuncture.

The Michaelis constant ($K_m$) for erythrocyte acetylcholinesterase activity under these conditions was 102.5 µM (SEM 29.6 µM) and $V_{max}$ was 9.2552 (SEM=0.6386)×$10^{-6}$ moles/gm/min against acetyl-β-methylthiocholine.

The Michaelis constant ($K_m$) was 190.9 µM (SEM 11.7 µM) for plasma butyrylcholinesterase with butyrylthiocholine. butyrylcholinesterase $V_{max}$ was 4.853 (SEM=0.135)× $10^{-6}$ moles/gram of plasma/min. The $K_m$ for erythrocyte acetylcholinesterase was 102.5 µM with acetyl-β-methylthiocholine. Acetylcholinesterase $V_{max}$ was 9.2552 (SEM=0.6386)×$10_{-6}$ moles/gram of erythrocytes/min.

Baseline erythrocyte acetylcholinesterase and plasma butyrylcholinesterase levels were established with repeated testing over several days. The subject then took 0.016, 0.032, 0.064, 0.1, 0.15, and 0.22 mg/kg methanesulfonyl fluoride, in that order, on a schedule of one dose Monday, Wednesday, and Friday over two consecutive weeks. Blood cholinesterase levels were assayed 4 hours after each dose and again immediately before the next dose. Blood samples were taken for clinical evaluations once each week.

Figure 2:
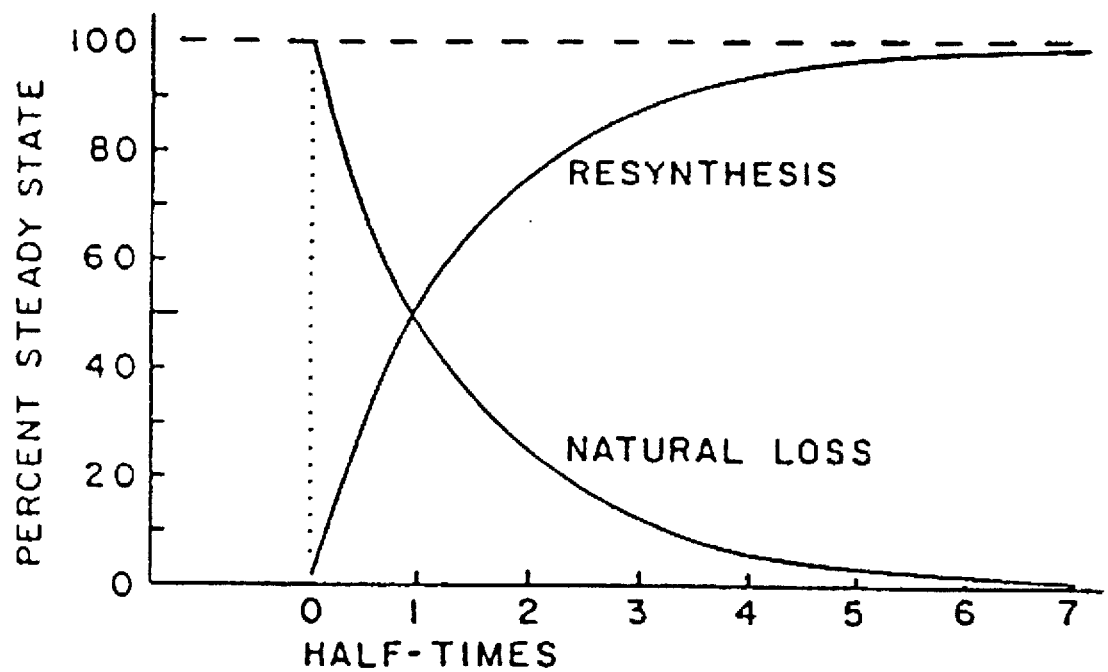
FIG. 2 shows the synthesis and loss of enzyme at steady state.
Figure 3:
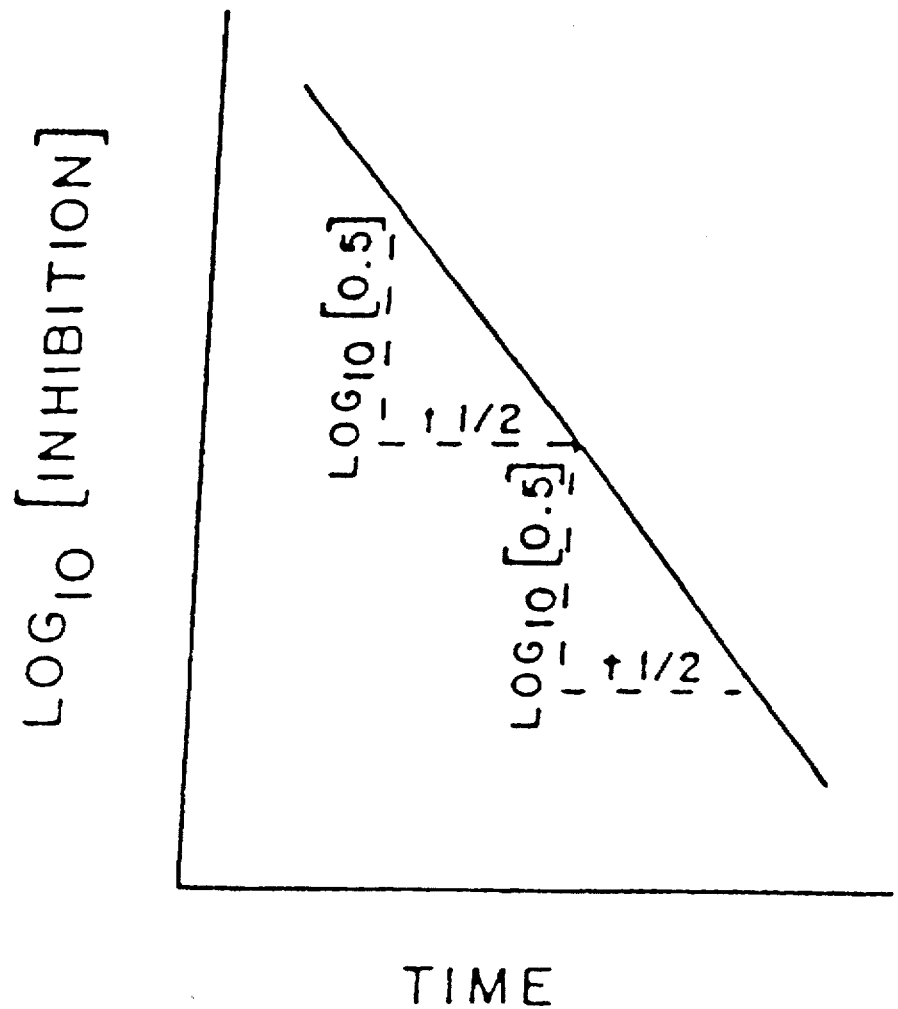
FIG. 3 shows an illustration of the pseudo-first order kinetic model.

The erythrocyte acetylcholinesterase and plasma butyrylcholinesterase results are shown in FIGS. 1 and 2, respectively. The recovery of erythrocyte acetylcholinesterase was followed for 80 days after the last dose and the results are shown in FIG. 3. The subject experienced no cholinergic effects (e.g., diarrhea, vomiting, nausea, etc.) and there were no changes of any type in the clinical blood analyses.

FIG. 1 shows that methanesulfonyl fluoride is active by oral administration and the effects of the drug can be monitored effectively from erythrocyte acetylcholinesterase inhibition. Analysis of the data from FIG. 1 shows that methanesulfonyl fluoride produced an orderly dose-response curve in spite of the very limited data obtained (one observation at each dose). The estimated minimum therapeutic dose from these data is 0.11 mg/kg.

The method of computing the minimum therapeutic dose, i.e., the dose that will produce 18% inhibition of the enzyme remaining active at the time each dose is administered, was calculated as described below. For the calculation of therapeutic dose and estimation of effect, the estimate of the therapeutic dose of methanesulfonyl fluoride, as an irreversible inhibitor, was based upon two assumptions. One is that each dose of methanesulfonyl fluoride produces a consistent percent inhibition of the enzyme that remains active at the time the dose is given. This means that the effect of each dose of methanesulfonyl fluoride will diminish as the level of active enzyme declines from prior doses. The second assumption is that erythrocyte acetylcholinesterase can be used to estimate the percent inhibition that occurs in the brain.

Kinetic theory of inhibition and the; orderly dose-response data obtained support the contention that the effects of methanesulfonyl fluoride can be predicted on the basis of inhibition of a percent of the enzyme that is active at the time each dose is given. Animal data support the second assumption that the increment in inhibition produced by each dose has about an equal effect in brain and erythrocyte acetylcholinesterase.

Calculations of the estimated therapeutic dose (i.e., one that will produce an asymptotic level of inhibition of more than 50%) can be completed using a pseudo-first-order kinetic model. The pseudo-first-order model can be deduced from an analysis of the steady state conditions which maintain a "normal" level of enzyme under non-drug conditions. Specifically, the rate at which new enzyme is synthesized by the tissues must be equal to the rate of normal enzyme loss. The rate of natural enzyme loss is based on the amount of active enzyme present and the pseudo-first order model will assume by definition that 50% of existing enzyme activity will be lost in one half-time. In contrast to enzyme loss, the rate of enzyme synthesis is a process with a constant capacity and the rate of new synthesis is constant. The system will reach a steady state condition when the rate of enzyme synthesis causes sufficient enzyme to accumulate in the tissues so that the rate of enzyme loss is equal to enzyme synthesis. The level of in vivo enzyme is a function of the balance between the constant rate of synthesis and the rate of enzyme loss. At the steady state balance, of course, the rate of synthesis will equal loss (the half-time for synthesis will equal the half-time for loss). The function of this system is illustrated in FIG. 2.

TABLE I

Steady State Kinetics
(No Inhibitor). Assume, for this example, normal = 1000 units (u):

| Natural Loss | New Synthesis | Amount Present | Inhibition |
|---|---|---|---|
| | At start . . . | 1000 units | 0% |
| 1 $t_{1/2}$ –50% enzyme present (–500 u) | +500 units | 1000 units | 0% |
| 2 $t_{1/2}$ –50% enzyme present (–500 u) | +500 units | 1000 units | 0% |
| 3 $t_{1/2}$ –50% enzyme present (–500 u) | +500 units | 1000 units | 0% |
| 4 $t_{1/2}$ –50% enzyme present (–500 u) | +500 units | 1000 units | 0% |

Steady state natural enzyme loss and natural new synthesis maintains normal enzyme levels.

Table I gives a numerical example under normal (non drug) conditions. The pseudo-first order kinetic of enzyme replacement after a drug dose producing 100% inhibition is shown in a numerical example in TABLE II.

TABLE II

Steady State Kinetics (Drug Produces 100% Inhibition)
Assume, for this example, that normal = 1000 units (u)

| Natural Loss* | New Synthesis** | Amount | Inhibition |
|---|---|---|---|
| | At start . . . | 1000 units | 0% |
| Drug administration produces 100% inhibition . . . | | 0 units | 100% |
| 1 $t_{1/2}$ –50% of enzyme present (–0 u) | +500 units | 500 units | 50% |
| 2 $t_{1/2}$ –50% of enzyme present (–250 u) | +500 units | 750 units | 25% |
| 3 $t_{1/2}$ –50% of enzyme present (–375 u) | +500 units | 875 units | 12.5% |
| 4 $t_{1/2}$ –50% of enzyme present (–437 u) | +500 units | 937 units | 6.25% |

*Natural loss at 50% of the enzyme present;
**New synthesis is a constant capacity unaffected by drug or amount of enzyme present.

In TABLE II, it can be seen that the enzyme recovery approaches the asymptotic level of 100% activity without additional drug treatments. The percent inhibition remaining after each half-time ($t_{1/2}$) can be calculated without reference to the constant rate of synthesis balanced against enzyme loss. The percent inhibition remaining at the end of each half-time can be estimated by multiplying the amount of enzyme inhibition remaining at the end of the previous half-time by 0.5. The amount of time required to reduce the amount of inhibition by a factor of 0.5 (one-half) is, of course, the definition of a half time. Therefore, when multiplying by a constant value, the easiest method for calculating changes over time is to convert the percent inhibition to $LOG_{10}$ [percent inhibition] and add the $LOG_{10}$ [0.5] to that value. In accordance with the rules of logarithms, this is the same as multiplying by 0.5 and the answer is the $LOG_{10}$ [percent inhibition] after the additional half-time. By converting to logarithms, therefore, a plot of $LOG_{10}$ [percent inhibition] against time becomes linear because the change in y-axis becomes the logarithm of 0.5 for each half time. This model explains the pseudo-first order recovery from enzyme inhibition that is actually observed after administration of an irreversible inhibitor as shown by a straight line when $\log_{10}$[%INH] is plotted against time. The pseudo-first order model will accurately predict recovery from methanesulfonyl fluoride-induced inhibition of acetylcholinesterase in tissues.

Using this model, the in vivo effects of methanesulfonyl fluoride can be predicted by using the straight line in the pseudo-first order model obtained by plotting $Log_{10}$ of percent of remaining inhibition against time (FIG. 3). The slope of the line, as with any straight line, is the change in y divided by the change in x. This translates into [$Log_{10}$ $0.5/t_{1/2}$], where $t_{1/2}$ is the half-time for resynthesis of 50% of the enzyme, a function of each tissue. Using this model, each dose of methanesulfonyl fluoride produces a change in the intercept (level of inhibition from which continuous recovery by resynthesis occurs) and the slope of the line from the intercept describes the recovery of activity (decrease in inhibition) as a function of time. It is also important to note that pseudo-first order kinetics progress according to this model regardless of the beginning point. In this application of pseudo-first order kinetics, brain recovery from methanesulfonyl fluoride-induced inhibition will follow the model regardless of level of inhibition at the beginning of recovery (i.e., the level of inhibition that remains after each drug dose). Using this model, asymptotic levels of inhibition produced by regular doses of methanesulfonyl fluoride can be computed given the percent of inhibition of remaining enzyme and the half-time for recovery for the tissue in question.

With the pseudo-first order model, enzyme levels can be estimated if only two variables are known: the half-time for the recovery of enzyme activity and the percent inhibition of remaining activity produced by each drug administration. Using this model, calculations show that a dose of methanesulfonyl fluoride that produces 18% inhibition of the remaining active enzyme three times per week will produce an asymptotic level of inhibition above 50%, the therapeutic window. These computations show the correlation between inhibition of brain acetylcholinesterase (half-time estimated at 12 days) and erythrocyte acetylcholinesterase (half-time estimated at 43 days).

The greatest uncertainty in using this model to predict the level of human brain inhibition produced by methanesulfonyl fluoride is the half-time of human brain acetylcholinesterase. It can be estimated to be between 10 and 14 days from experiments in rats and monkeys but it cannot be determined in humans without repeated biopsies of cortex. Therefore, the estimate of 12 days is used with recognition that this is an uncertain estimate. To assess the consequences of an erroneous estimate of human brain acetylcholinesterase, computations were made using estimated half-times of 10, 12, 14, 16, and 18 days. In addition, the effects of various doses of methanesulfonyl fluoride including inhibition of 12%, 14%, 16%, and 18% with each dose given three times per week were included in these calculations.

In any straight line function, the slope of the line is the change in Y (LOG10[Percent Inhibition]) divided by the change in X (half-times). In this application, by definition, there is a reduction of inhibition by half (0.5) with each half-time. Therefore, the slope of this line is the logarithm of 0.5 (−0.301) divided by the half-time.

The heading "Produced with each Dose" should be moved to the left over the center column of 12% ... 18% indicators of dose effects. "Percent Inhibition" that now appears on line 5 should be over the ranges of percent inhibition on the right-most column in the table. "Percent Inhibition" could also be changed to "Asymptotic Percent Inhibition" to be more clear. I have a hand-drawn Figure that could be substituted for this rather confusing Table.

TABLE III

Estimates of Asymptotic Inhibition of Brain acetylcholinesterase as a Function of Dose and Half-Time of Enzyme Resynthesis

| Half-Time (days) | Produced with each dose | Asymptotic Percent Inhibition** |
|---|---|---|
| 10 | 12% | 42–48% |
|    | 14% | 46–53% |
|    | 16% | 49–57% |
|    | 18% | 52–60% |
| 12 | 14% | 50–57% |
|    | 16% | 54–60% |
|    | 18% | 57–64% |
| 14 | 12% | 51–56% |
|    | 14% | 54–61% |
|    | 16% | 57–64% |
|    | 18% | 62–68% |
| 16 | 14% | 58–63% |
|    | 16% | 62–67% |
|    | 18% | 64–71% |
| 18 | 12% | 57–62% |
|    | 14% | 61–66% |
|    | 16% | 63–70% |
|    | 18% | 67–73% |

*Based on oral dose given three times per week, percent inhibition is based on the amount of enzyme that is active at the time of each dose. Asymptotic level of inhibition was calculated from the pseudo first-order model given above.
**Range given is the estimated high and low level of enzyme activity which includes recovery by new synthesis according to the half-time indicated in each entry in the Table. The Therapeutic Dose is generally estimated to be a minimum of 50% inhibition.

Table III shows that a dose of methanesulfonyl fluoride that produces 16% or 18% inhibition will be sufficient to produce at least 50% asymptotic level of inhibition if the half-time for the brain acetylcholinesterase is as short as 10 days. However, a dose of methanesulfonyl fluoride producing 14%, 16%, or 18% inhibition three times per week will produce an asymptotic level of inhibition of more than 50% if the half-time for brain acetylcholinesterase is 12 days. If the half-time for human brain acetylcholinesterase is as long as 18 days, a dose that produces as little as 12% inhibition given three times per week will produce as asymptotic level of inhibition of more than 50% and a dose that produces 18% inhibition will produce an asymptote of about 70%.

Using the results of calculations shown in Table III, based on dosing three times per week, it appears reasonable to use a dose of methanesulfonyl fluoride that produces at least 18% inhibition of remaining active enzyme each time it is given with the estimated half-time of 12 days. This will produce the therapeutic window of more than 50% inhibition with any brain half-time of 10 through 18 days. The consequences of the uncertainty of human brain half-time, although troubling, are not insurmountable.

EXAMPLE 5

Dosing Schedule

The dosing schedule of three times per week is an important part of the treatment strategy. Methanesulfonyl fluoride is highly soluble in lipids and, once it is solubilized in brain membranes, it continues to react against acetylcholinesterase even after it is removed from the aqueous environment of the membranes in vitro. The lipid solubility of methanesulfonyl fluoride is probably why it produces much more inhibition in brain than peripheral tissues. The therapeutic strategy with an irreversible inhibitor such as methanesulfonyl fluoride is, therefore, to give small doses from time-to-time that are selectively taken into the brain lipids. The methanesulfonyl fluoride concentration in the peripheral blood drops within hours and methanesulfonyl fluoride is not present in blood in sufficient concentrations to continue to produce inhibition in peripheral tissues or be a metabolic load for liver detoxification. The effects of methanesulfonyl fluoride, therefore, accumulate in brain because of the long half-life for resynthesis and the initially higher level of inhibition. These advantages would be essentially lost with frequent or continuous administrations of methanesulfonyl fluoride. Doses given three times per week strike a balance between going too long between doses so that too much resynthesis takes place and losing the pharmacokinetic advantages of infrequent administrations.

Figure 4:
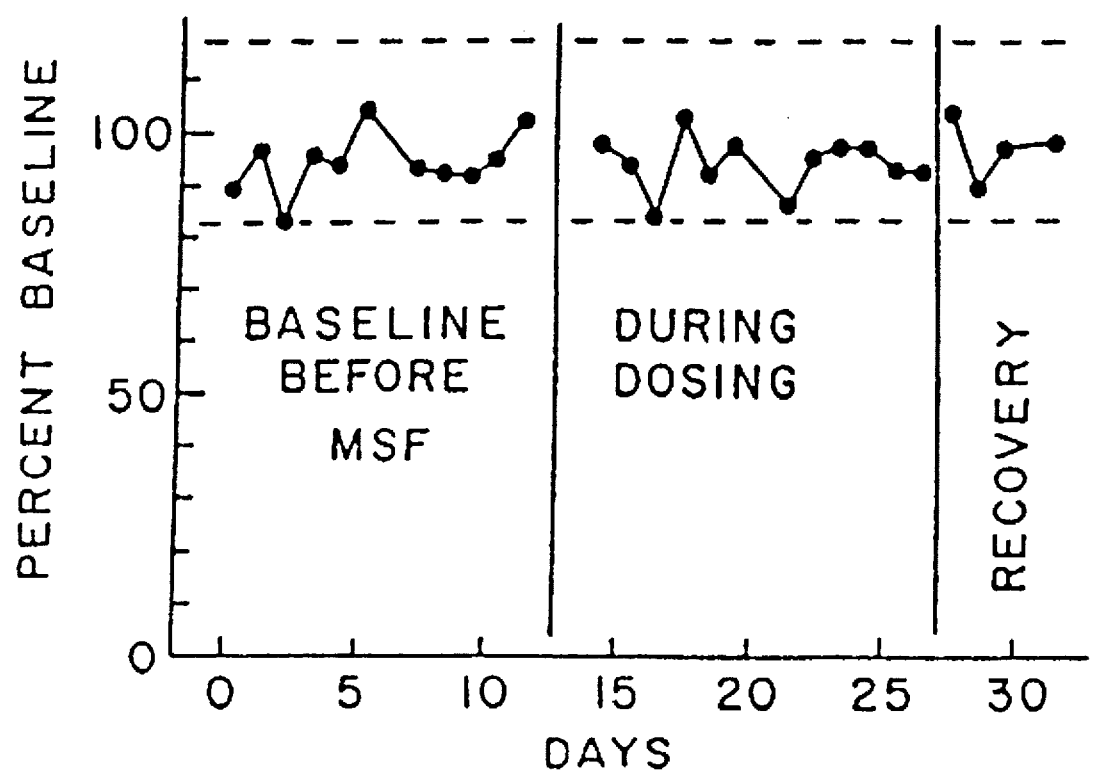
FIG. 4 shows the effects of methanesulfonyl fluoride on plasma butyrylcholinesterase.

FIG. 4 shows that the effect of methanesulfonyl fluoride is strongly selective for erythrocyte acetylcholinesterase as there was virtually no inhibition of plasma butyrylcholinesterase at these doses. These results confirm similar selectivity as an acetylcholinesterase inhibitor was also recently shown in human brain enzyme studies.

Figure 5:
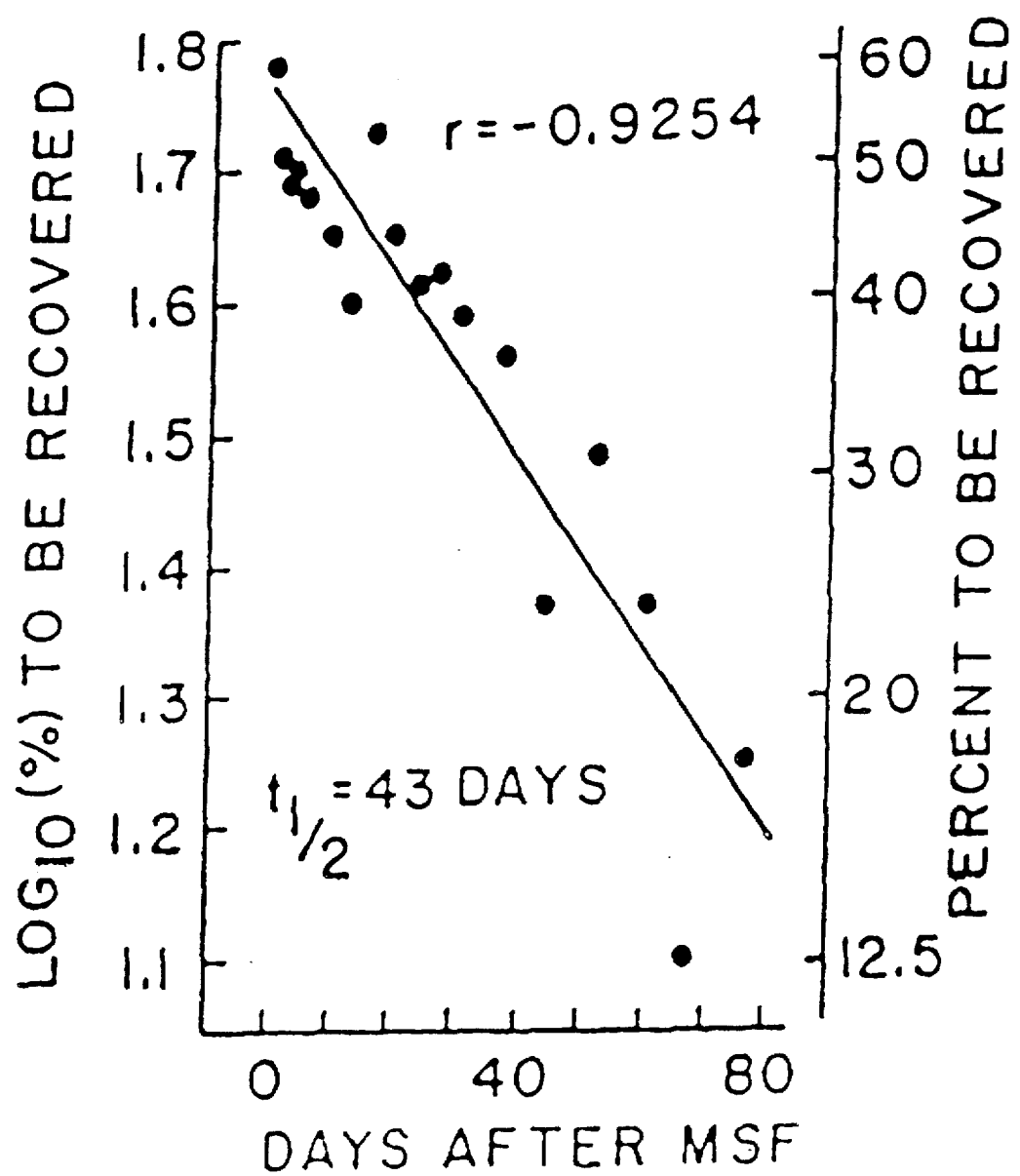
FIG. 5 shows the recovery of erythrocyte acetylcholinesterase.

FIG. 5 shows that recovery of erythrocyte acetylcholinesterase activity in blood follows pseudo-first order kinetics (i.e., a plot of $LOG_{10}$ [% inhibition] is linear with time, r=−0.9254 computed with least squares linear regression). FIG. 5 shows that the half-life for the recovery of erythrocytes was 43 days, a figure that is consistent with other reports of erythrocyte half-life and one used in the experiments described above to estimate asymptotic levels of erythrocyte acetylcholinesterase inhibition that are required to correlate with therapeutic effects in the brain.

The following additional information about erythrokinetics related to the validity of using erythrocyte acetylcholinesterase to estimate therapeutic effects of methanesulfonyl fluoride is provided. The estimation of the effects of methanesulfonyl fluoride by using erythrocyte acetylcholinesterase depends, in large part, on erythrokinetics. If methanesulfonyl fluoride or other irreversible inhibitors of erythrocyte acetylcholinesterase affect erythropoiesis or the survival of erythrocytes, there could be serious consequences. First of all, any drug that affects erythropoiesis could have serious physiological consequences related to disturbance of normal erythrocyte functions. In addition, however, estimates of level of inhibition would be severely affected. This type of error could cause serious misjudgment of level of inhibition and produce toxic consequences if the error led to overtreatment.

The stability of erythropoiesis with chronic inhibition of acetylcholinesterase has been studied in humans. The function of acetylcholinesterase in the primitive and mature erythroid is unknown but it has been suggested that acetylcholinesterase may have a role in differentiation. However, with chronic inhibition of up to 82% of erythrocyte acetylcholinesterase for up to 7 months in 18 patients with SDAT, there were no changes in erythrocyte, leukocyte or platelet characteristics or numbers. This suggests that chronic acetylcholinesterase inhibition does not have deleterious effects on erythropoiesis. In the treatments of the present invention, there were no changes in hematocrit in patients treated with methanesulfonyl fluoride up to 8 weeks with 85–90% inhibition of erythrocyte acetylcholinesterase.

The second question is whether or not inhibition of erythrocyte acetylcholinesterase affects the survival of mature erythrocytes present in blood. The role of acetylcholinesterase in the mature erythrocyte is unknown. However, it is located in the surface of the erythrocyte and the rate-limiting process for the replacement of erythrocyte acetylcholinesterase is the production of new erythrocytes. Under normal conditions, the erythrocytes have a full-life span of 83–120 days although there are methods for labeling erythrocytes that give erroneously shorter estimates of the life-span. Although it has been proposed that erythrocytes are replaced at a constant rate of 0.8 to 1.2 percent per day in humans, under steady state conditions existing with chronic inhibition of acetylcholinesterase, the appearance of new erythrocyte acetylcholinesterase with the production of new erythrocytes will follow pseudo-first order kinetics. This is shown by the strictly linear plot of $LOG_{10}$ [%INH] against time shown in FIG. 5 showing recovery of erythrocyte acetylcholinesterase for 80 days after methanesulfonyl fluoride treatment ceased. The erythrocyte half-life of 43 days (corresponding to a full-life span of 86 days) calculated from those data agrees well with other estimates of erythrocyte full-life spans of 83 to 120 days. Furthermore, erythrocyte acetylcholinesterase returned to normal in all humans given di-isopropyl fluorophosphate (DFP) if they were studied for a sufficient time after the cessation of DFP and these individuals showed no evidence of resistance or sensitization to additional administrations of the drug. Individual differences in blood cholinesterases (both erythrocyte acetylcholinesterase and plasma butyrylcholinesterase) cannot be correlated with age, sex, weight, menstrual cycle, diet, exercise, or moderate fasting. Lastly, there is clear evidence that inhibition of erythrocyte acetylcholinesterase does not affect erythrocyte survival.

In summary, it appears that monitoring erythrocyte acetylcholinesterase is a method of monitoring the accumulated effects of methanesulfonyl fluoride treatment. It is important to note, however, that there is no direct correlation between erythrocyte acetylcholinesterase accumulated inhibition and CNS acetylcholinesterase accumulated inhibition. The estimation of CNS inhibition from erythrocyte inhibition must be made from calculations based on estimated differences in half-life of the enzyme in each tissue and knowledge of treatment history (size and temporal spacing of doses).

EXAMPLE 6

Experiment II

Experiment II was a Phase I trial of methanesulfonyl fluoride in a group of 10 normal subjects. These subjects were recruited from an educational group of 13 normal healthy persons who met at Centro Medico Geriatrico on a weekly basis. One person declined to participate and 12 began the protocol. Two persons were lost from the group from causes unrelated to the drug (business trips). Ten people completed the protocol. This group consisted of 7 females and 3 males with an average age of 45.8 years (SD 6.7 years, range from 38 to 60 years) weighing an average of 75.45 Kg (SD 9.8 Kg, range from 63.5 to 98 Kg). All were free of other medications, had normal clinical blood profiles and EKG, and gave informed consent.

Baseline erythrocyte acetylcholinesterase levels were established by triplicate assays using procedures described above on all subjects before drug administration. All assays were conducted with 1.0 mM acetyl-β-methyl thiocholine substrate, approximately 10 times $K_m$. This substrate concentration produces about 91% of $V_{max}$ without substrate inhibition. Changes in estimated $V_{max}$ are the best measures of the effects of irreversible inhibitors such as methanesulfonyl fluoride.

Methanesulfonyl fluoride was given in doses of 0.03, 0.06, 0.12, 0.18, 0.18, and 0.18 mg/kg in that order on a schedule of three doses per week. Three doses per week was also to be used in treating patients because of the long duration of action of methanesulfonyl fluoride. The doses were selected to begin below and then increase to 150% of the expected therapeutic dose.

Accumulated inhibition of erythrocyte acetylcholinesterase was estimated by a blood sample taken by finger prick before each dose according to the procedures described above. Because plasma butyrylcholinesterase showed no inhibition in the experiments described above, those assays were deleted from the protocol. An interview was conducted three times per week, at the time of the next dose and erythrocyte acetylcholinesterase assay, to document any side effects.

Figure 6:
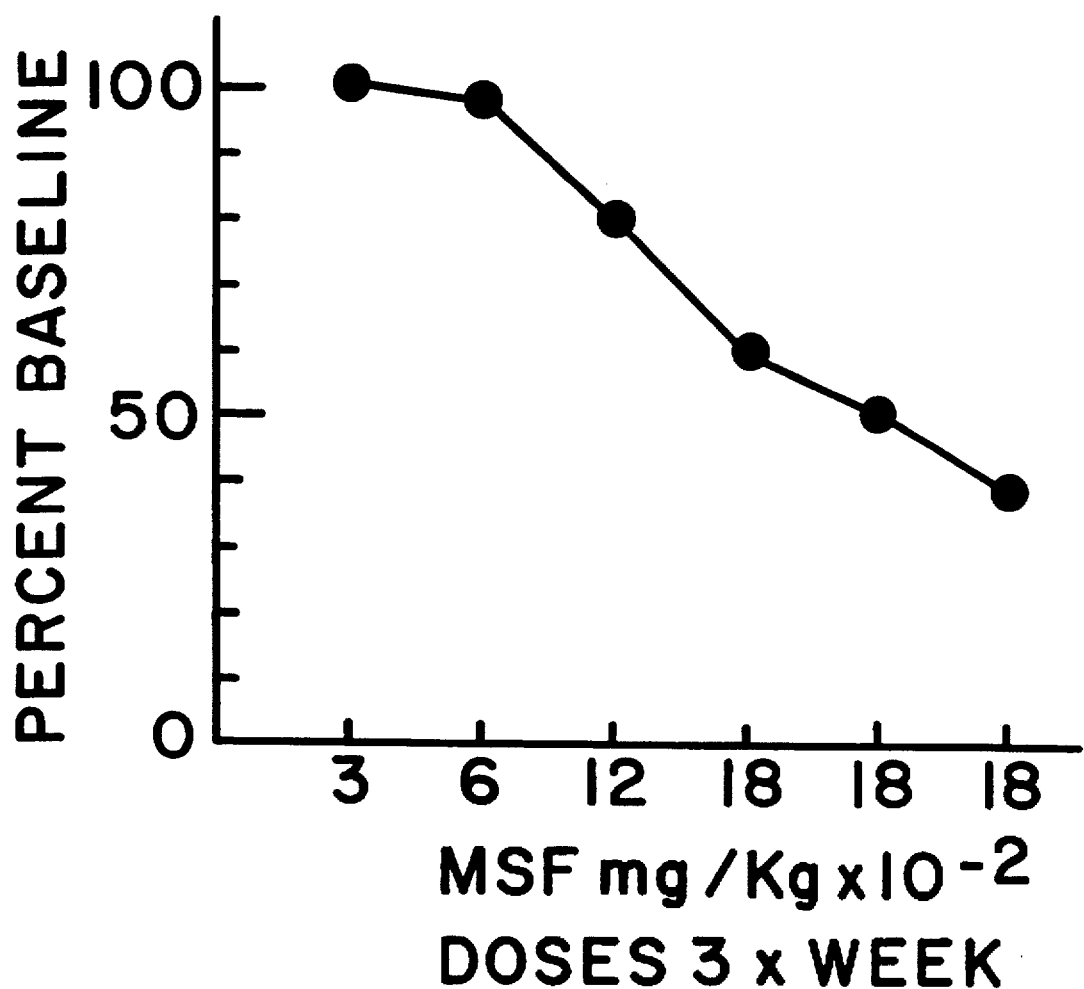
FIG. 6 shows the cumulative erythrocyte acetylcholinesterase inhibition.

Mean accumulated erythrocyte acetylcholinesterase inhibition observed in this group is shown in FIG. 6. A dose-response analysis of these results by least squares linear regression (r=+0.8956) gives the dose/response function:

$$\%INH = (39.9944)(LOG_{10}[Dose\ mg/kg]) + 51.718$$

Using this function, the dose required to produce 18% inhibition of acetylcholinesterase remaining active at the time of each dose is 0.143 mg/kg.

FIG. 6, which shows a linear dose/response function, confirms that there is an orderly and consistent dose/response relationship. Methanesulfonyl fluoride is consistently absorbed after oral administration with consistent and predictable results. All doses used were tolerated well.

Based on the methods described above and the data from FIG. 6, a refined estimation of the therapeutic dose (that which will produce 18% inhibition of remaining enzyme with drug administration three times per week) is 0.14 mg/kg, only slightly higher than that estimated from only one case in Experiment I. Thus, on the basis of results from Experiments I and II that methanesulfonyl fluoride is safe at the range of doses expected to produce a therapeutic effect in the treatment of dementia. The minimum therapeutic dose to be used was determined to be 0.14 mg/kg with the option of increasing the dose to 0.18 mg/kg without unacceptable risks of toxicity.

EXAMPLE 7

Experiment III

The following experiment demonstrated the safety and efficacy of methanesulfonyl fluoride in patients suffering from SDAT. The criteria for inclusion included patients with cognitive deterioration in two areas, in addition to memory, without a specific etiological factor that can be demonstrated by clinical history or supporting examinations (EEG, VDRL, HIV, endocrinology, liver or kidney dysfunction, or a deficiency of $B_{12}$) that can explain pathophysiologically the dementia syndrome. Further selection was based on Spanish translations of the following: (1) a score of 3-5 on the Global Dementia Scale (GDS) of Reisberg; (2) a score of 12-26 on the Mini Mental State Exam (MMSE) of Folstein; (3) a score of less than 11 on the Geriatric Depression Scale (GDS); (4) a Hachinski score of less than 5; and an arterial blood pressure of no more than 1 80/100.

The criteria for exclusion included (1) a history of psychiatric illness defined by the DSM IV which preceded the dementia syndrome; (2) associated neurological or clinical illness (e.g., extrapyramidal disorders at onset); (3) History of previous cerebrovascular illness; (4) hypertension greater than 180/100; (5) previous abuse of alcohol or drugs of addiction; (6) GDS: 1-2 and 6-7; (7) MMSE >26 and <12; (8) Geriatric Depression scale score >11; (9) Hachinski >5; (10) liver pathology; (11) patient in a protocol for another experimental drug for the treatment of SDAT. Informed consent was obtained and a full clinical history was taken and evaluated.

Twenty one patients were enrolled in the study with intent to treat. Of those, 15 patients finished the protocol. No patients left the protocol because of a drug-related adverse event. Of the six patients who left the protocol, three were unable to complete the protocol because of transportation problems, one patient left Chihuahua to live in the U.S., one patient suffered from colitis before enrollment, during placebo and methanesulfonyl fluoride treatment and elected to leave the protocol, and one patient was noncompliant.

The 15 patients who completed the protocol were 5 men and 10 women with the following actual characteristics: (1) mean age 69.73 years (SD=7.4, range 60-82 years); (2) mean Mini-Mental State 16.67 points (SD=4.5, range 9-24); (3) mean Global Deterioration score 4.4 (SD=0.83, range 3-6); (4) mean Alzheimer's Disease Assessment Scale (Cognitive) score of 30.38 errors (SD=14.3, range 9-62)

EXAMPLE 8

Clinical Evaluation

The main outcome measures used to evaluate efficacy of methanesulfonyl fluoride were changes in the Alzheimer's Disease Assessment Scale-Cognitive subscale (ADAS-COG), Mini-Mental State Exam (MMSE), Global Deterioration Scale, and the Clinical Interview Based Impression of Change (CIBIC). The patients were evaluated at entry into the protocol (baseline), after the first 8 weeks of treatment (methanesulfonyl fluoride or placebo), and at the end of the 16 week protocol (after 8 additional weeks of placebo or methanesulfonyl fluoride). The patients, the families, and the investigators conducting the clinical evaluations were blind with regard to treatment throughout the protocol. All patients were subjected to regular clinical blood testing to measure toxicity throughout the protocol and at the end of the protocol.

EXAMPLE 9

Methanesulfonyl Fluoride Dosing and Treatment Schedule

The results above indicated that 0.14 mg/kg is the minimum dose required to produce the therapeutic effect (minimum of 50% asymptotic inhibition of acetylcholinesterase in the brain) when given on a schedule of three times per week. Patients were started on a test dose sequence of 0.03, 0.07 mg/kg and then administered 0.14 mg/kg three times per week for the first 4 weeks of the 8 weeks of treatment in the protocol. The first 7 patients in the protocol also received 0.14 mg/kg during the second 4 weeks of the 8 weeks of treatment. Because there were no adverse events at 0.14 mg/kg in the first 7 patients, the last 8 patients received 0.18 mg/kg during the second 4 weeks of methanesulfonyl fluoride treatment. Except for dosage, drug and drug preparation procedures were as described above. The effects of methanesulfonyl fluoride were monitored by assays of erythrocyte acetylcholinesterase conducted according to the spectrophotometric method of Ellman et al. described above. No assays of methanesulfonyl fluoride effects on plasma butyrylcholinesterase were conducted.

EXAMPLE 10

Experimental Design

The experimental design was random assignment of subjects in a double blind crossover experiment with placebo control. Some patients received methanesulfonyl fluoride the first 8 weeks (Group A) and others received placebo the first 8 weeks (gelatin capsules with oil) first (Group B). In the crossover, the second 8 weeks, the patients who received methanesulfonyl fluoride received placebo and visa-versa. There were two basic statistical evaluations: 1) improvement or deterioration during the placebo period (8 weeks) compared with improvement or deterioration during the methanesulfonyl fluoride period (8 weeks); and 2) analysis of performance relative to baseline (entry into the protocol). The student's t-test for paired observations was used for the initial test of significance comparing placebo to methanesulfonyl fluoride performance for each subject (paired scores, within subjects). Because of the very small sample, the results obtained with this t-test were confirmed with the Wilcoxon Matched-Pairs Signed Ranks Test. For a comparison of patients who received methanesulfonyl fluoride/ placebo (Group A, N=9) with patients who received placebo/ methanesulfonyl fluoride (Group B, N=6), the Wilcoxon Rank-Sum Test was used for this between groups comparison [27]. The difference in size between Group A and Group B was caused by randomly losing more patients from the protocol who started on placebo than patients who started on methanesulfonyl fluoride. All significance was estimated from one-tailed tests (i.e., only improvement predicted).

EXAMPLE 11

Methanesulfonyl Fluoride Dosing and Treatment

The activity of methanesulfonyl fluoride as an inhibitor of acetylcholinesterase after oral administration given three times per week was clearly shown by obtaining and maintaining a mean level of 85.35% (SEM=2.5%) inhibition of erythrocyte acetylcholinesterase after treatment with 0.14 mg/kg methanesulfonyl fluoride. In those patients who received 0.18 mg/kg, 89.53% (SEM=1.07%) inhibition was obtained and maintained.

Although there is not a direct correlation between inhibition of brain and erythrocyte acetylcholinesterase, calculations based on the estimated difference in the half-life of erythrocyte acetylcholinesterase compared to brain acetylcholinesterase can be used to estimate inhibition of brain acetylcholinesterase. According to these calculations, this methanesulfonyl fluoride treatment was sufficient to produce well over 50% asymptotic inhibition in the brain and illustrates the clinical efficacy of methanesulfonyl fluoride in the treatment of dementia.

There were no adverse events related to drug treatment and no patients suffered from nausea, vomiting, diarrhea, or other cholinergic side effects. There were no changes in clinical blood profiles, especially transaminases and there were no signs of methanesulfonyl fluoride toxicity at the doses used.

EXAMPLE 12

Cognitive Performance

Figure 7:
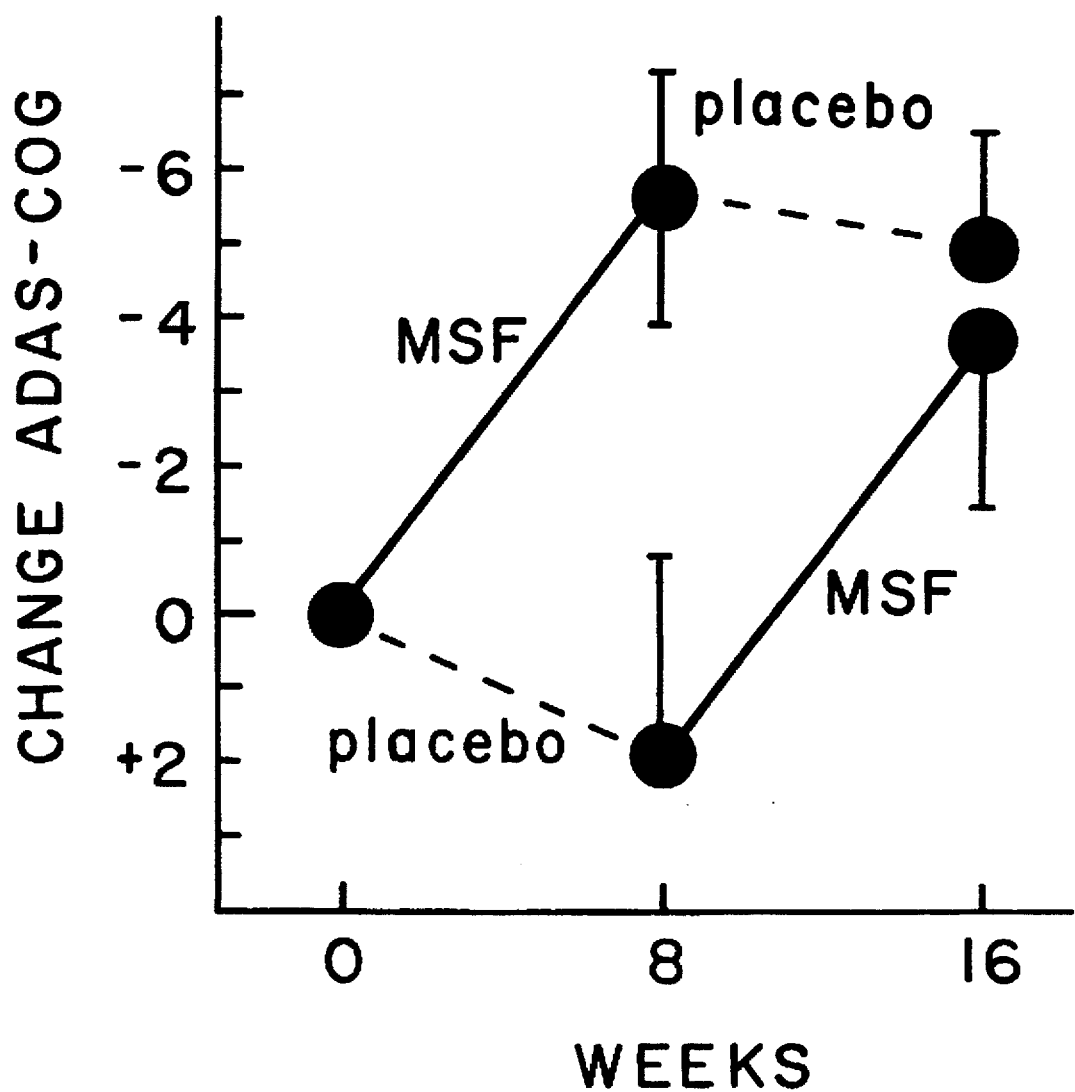
FIG. 7 shows the performance on ADAS-COG throughout 16 Week Protocol. Performance on placebo is shown in dashed lines while performance on methanesulfonyl fluoride is shown in solid lines.

FIG. 7 shows the overall cognitive performance of the patients in Experiment II as measured by the ADAS-COG. The group of patients who received methanesulfonyl fluoride in the first eight weeks of the protocol followed by placebo and plotted separately from the group of patients who received placebo in the first eight weeks followed by methanesulfonyl fluoride for the last eight weeks.

As shown in FIG. 7, there was substantial improvement of cognitive performance (reduction in errors on the ADAS-COG) during methanesulfonyl fluoride treatment and a slight decline in performance (increase in errors) during the 8 week placebo phase. It is particularly interesting to note that the group which received methanesulfonyl fluoride treatment in the first 8 week period showed only a small decline in performance during the subsequest placebo treatment. It was expected that these patients would decline to the beginning scores (a change to zero or below) because the direct effects of methanesulfonyl fluoride would be expected to have ended after 8 additional weeks of placebo (no methanesulfonyl fluoride treatment). Therefore, in view of the strong methanesulfonyl fluoride-induced improvement, a large decline in performance was expected during placebo in those patients who received methanesulfonyl fluoride first. There was an unexpectedly strong carry-over effect of methanesulfonyl fluoride treatment. Those patients who received placebo second in the protocol, maintained virtually all improvement (about 6 points) throughout 8 additional weeks of placebo treatment.

To more carefully analyze the change during methanesulfonyl fluoride treatment as shown in FIG. 7, the change in cognitive performance during methanesulfonyl fluoride was combined without regard to whether or not methanesulfonyl fluoride was received first or second in the protocol.

Figure 8:
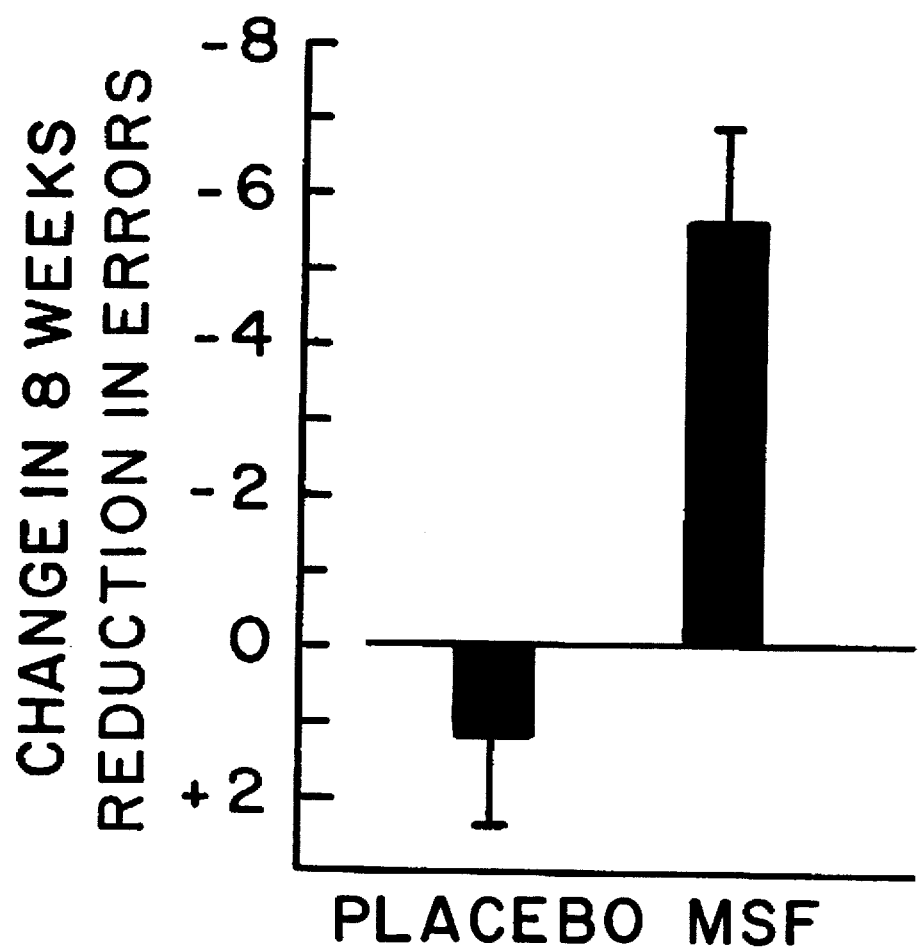
FIG. 8 shows the reduction in errors in the ADAS-COG test after eight week periods after either placebo control or methanesulfonyl fluoride.
Figure 9:
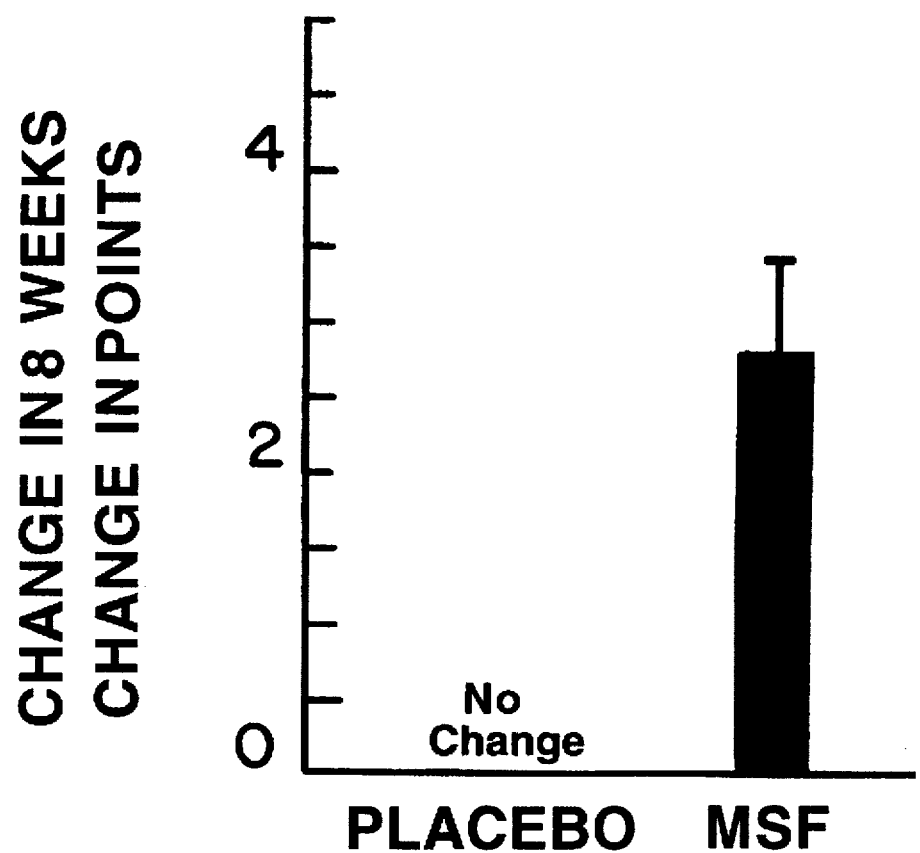
FIG. 9 shows the change in points in the Mini Mental State Exam after eight week periods after either placebo control or methanesulfonyl fluoride.

Similarly, the change in cognitive performance during placebo was combined without regard to whether placebo was received first or second in the protocol. The data were calculated by a difference score based on the cognitive performance of the patient at the beginning of each 8 week period with performance at the end of each 8 week period (FIGS. 8 and 9). Each patient had one difference score for placebo and one difference score for methanesulfonyl fluoride treatment. FIG. 8 shows improvement as measured by the ADAS-COG (decrease in errors) and FIG. 9 shows improvement as measured by the MMSE (increase in points).

A statistical comparison of change in performance in 8 weeks on methanesulfonyl fluoride with change in performance in 8 weeks on placebo as measured by the ADAS-COG showed that methanesulfonyl fluoride produced significant improvement compared to the placebo ( $p<0.01$ one-tailed on both the paired t-test and the Wilcoxon Matched-Pairs Signed-Ranks Test). Similarly, as measured by improvement in Mini-Mental State scores, methanesulfonyl fluoride produced significant improvement compared to the placebo ($p<0.01$ one-tailed on both the paired t-test and the Wilcoxon Matched-Pairs Signed-Ranks Test).

Because of the very strong carry-over effects shown in FIG. 7, it was not possible to separate placebo and methanesulfonyl fluoride effects on the CIBIC and Global Deterioration scores in this number of patients with these relatively variable subjective measures. Therefore, the ratings on these measures at the end of the completed 16 week protocol were compared with baseline ratings at the beginning of the protocol.

At the beginning of the protocol, all patients are assigned a CIBIC rating of 4.0; improvement in condition is rated as 3, 2, or 1 while deterioration is rated 5, 6, or 7. Patients at the end of the protocol had a mean CIBIC of 2.98 (SD= 1.13), indicating significant improvement ($p<0.01$, t-test one-tailed). At the beginning of the protocol, the mean Global Deterioration Score was 4.4 (SEM=0.21) while at the end of the protocol the mean score was 3.1, a mean improvement of 1.3 (SEM=0.33) on this scale ($p<0.01$, t-test one-tailed).

In general, the greatest improvement was observed in the most severely demented patients in the protocol. Overall, improvement on ADAS-COG was correlated +0.6 ($p<0.05$, N=15) with ADAS-COG errors upon entering the protocol, indicating that the more errors the patient made in the baseline evaluation, the greater the improvement.

Methanesulfonyl fluoride doses sufficient for treatment of dementia were not accompanied by peripheral cholinergic or other toxic effects. This is because of the strong selectivity of methanesulfonyl fluoride for the CNS and its selectivity as an inhibitor of acetylcholinesterase. In addition, the improvement observed after treatment with methanesulfonyl fluoride was of relatively long duration, still clearly present after 8 weeks of placebo treatment.

The results obtained with methanesulfonyl fluoride suggest that methanesulfonyl fluoride is less toxic than tacrine (Cognex®, Parke-Davis). In a recent controlled trial with high dose tacrine, about 60% of the patients failed to complete the protocol because of adverse events related to drug toxicity. The adverse events related to tacrine treatment are cholinergic side effects (nausea, vomiting, diarrhea, etc.) and liver toxicity.

Two patients treated with methanesulfonyl fluoride had prior adverse effects from attempting tacrine treatment. One had experienced liver toxicity (and had recovered normal transaminase values before methanesulfonyl fluoride treatment) and the other experienced vomiting that limited the dose of tacrine to only 60 mg/day (an ineffective dose). Neither of these patients with known sensitivities experienced adverse events on methanesulfonyl fluoride.

Methanesulfonyl fluoride also appears to have significantly greater efficacy than tacrine in enhancing cognitive functions in SDAT. In the recent controlled trial with high dose tacrine, the 40% of the patients who could tolerate tacrine had a mean improvement of only 2 points on the ADAS-COG. In the present clinical trial of methanesulfonyl fluoride, there was a mean improvement of 6 points. Given that the patients had a mean of 30 errors on the ADAS-COG at the beginning of the protocol, a 6 point reduction is 20% improvement on this measure.

An additional finding of the present invention was the unexpectedly long duration of the methanesulfonyl fluoride-induced cognitive enhancement. Although the exact half-life of human brain acetylcholinesterase (the time it takes for resynthesis of 50% of the inhibited enzyme) is unknown and cannot be determined without repeated biopsies from humans, an estimate of 10–14 days can be generalized from rodent and monkey brain. Using this estimate for the human brain acetylcholinesterase half-time, the patients should have had less than 50% inhibition remaining after 10–14 days regardless of the level of inhibition existing at the end of methanesulfonyl fluoride treatment. Therefore, they should have been out of the therapeutic window (e.g., have less than 50% inhibition) in 10–14 days after methanesulfonyl fluoride treatment. It is clear from the data shown in FIG. 9, however, that methanesulfonyl fluoride-induced enhancement was maintained through 8 weeks of placebo in those patients who received methanesulfonyl fluoride first in the protocol. In conclusion, methanesulfonyl fluoride is novel, safe, and effective treatment of senile dementia of the Alzheimer type.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A pharmaceutical composition, comprising a sulfonyl fluoride and an agent selected from the group consisting of RS86, 4AP, and lecithin and a pharmaceutically acceptable carrier.

2. The pharmaceutical composition of claim 1, wherein said sulfonyl fluoride is selected from the group consisting of methanesulfonyl fluoride, phenylmethanesulfonyl fluoride, 3-amino-4-methylbenzenesulfonyl fluoride, 4-methoxymetanilyl fluoride, and ethanesulfonyl fluoride, benzenesulfonyl fluoride, paratoluenesulfonyl fluoride, 3-amino-4-ethoxybenzenesulfonyl fluoride, 3-amino-4-chlorobenzenesulfonyl fluoride, and isopropylsulfonyl fluoride.

3. The pharmaceutical composition of claim 1, wherein said sulfonyl fluoride is contained in said composition in an amount of from about 20 mg/ml to about 100 mg/ml.

4. The pharmaceutical composition of claim 1, wherein the pharmaceutically acceptable carrier is selected from the group consisting of USP/NF approved vegetable oil consisting of peanut oil, sesame oil, sunflower seed oil, wheat germ oil and synthetic oils.

5. A method of treating Alzheimer's disease in a human, comprising the step of administering to said human a therapeutically effective dose of a sulfonyl fluoride selected from the group consisting of methanesulfonyl fluoride and ethanesulfonyl fluoride.

6. The method of claim 5, wherein said dose of sulfonyl fluoride is from about 0.15 mg/kg to about 0.5 mg/kg.

7. The method of claim 5, wherein said sulfonyl fluoride is administered in a pharmaceutically acceptable excipient.

8. The method of claim 5, further comprising co-administering with said sulfonyl fluoride, a therapeutically effective dose of an agent selected from the group consisting of RS86, 4AP and lecithin.

9. A method of enhancing cognitive performance in an individual, comprising the step of administering to said individual a therapeutically effective dose of a sulfonyl fluoride selected from the group consisting of methanesulfonyl fluoride and ethanesulfonyl fluoride.

10. The method of claim 9, wherein said dose of a sulfonyl fluoride is from about 0.15 mg/kg to about 0.5 mg/kg.

11. The method of claim 9, wherein said methanesulfonyl fluoride is administered in a pharmaceutically acceptable excipient.

12. The method of claim 9, further comprising co-administering with said methanesulfonyl fluoride, a therapeutically effective dose of an agent selected from the group consisting of RS86, 4AP and lecithin.

13. The method of claim 9, wherein said individual has Parkinson's disease, Parkinsons dementia complex of Guam, Boxer's dementia, normal age-related memory impairment and a disorder characterized by insufficient acetylcholine in the central nervous system.

* * * * *

(12) REEXAMINATION CERTIFICATE (4587th)
United States Patent
Moss

(10) Number: US 5,798,392 C1
(45) Certificate Issued: Jun. 4, 2002

(54) SULFONYL FLUORIDES FOR THE TREATMENT OF ALZHEIMER'S DISEASE

(75) Inventor: Donald Eugene Moss, El Paso, TX (US)

(73) Assignee: The Board of Regents of the University of Texas System, Austin, TX (US)

Reexamination Request:
No. 90/005,873, Dec. 6, 2000

Reexamination Certificate for:
Patent No.: 5,798,392
Issued: Aug. 25, 1998
Appl. No.: 08/705,858
Filed: Aug. 28, 1996

(51) Int. Cl.$^7$ .................... A61K 31/135; A61K 31/10
(52) U.S. Cl. ........................ 514/649; 514/709
(58) Field of Search .................. 514/649, 709

(56) References Cited

FOREIGN PATENT DOCUMENTS

SU 657920 4/1979 ......... C07C/143/70

OTHER PUBLICATIONS

Becker, R.E., Colliver, J.A., Markwell, S.J., Moriearty, P.L., Unni, L.K., and Vicari, S. Double–Blind, placebo–controlled study of metrifonate, an acetylcholinesterase inhibitor, for Alzheimer disease. Alzheimer Disease and Associated Disorders 10(3): 124–131, 1996.

Palacios–Esquivel, R., Pacheco, G, and Moss, D.E. Methanesulfonyl fluoride (MSF) blocks scopolamine–induced amnesia in rats. Neurobiology of Aging 14, 93–96, 1993.

Moss, D.E., Kobayashi, H., Pacheco, G., Palacios, R., and Perez, R.G. Methanesulfony fluoride: A CNS selective cholinesterase inhibitor. In: Current Research in Alzheimer Therapy: Cholinesterase Inhibitors, E. Giacobini and R. Becker (Eds.), Taylor and Francis, New York, 1988. pp. 305–314.

Moss, D.E., Rodriguez, L.A., Herndon, W.C., Vincenti, S.P. and Camarena, M.L. Sulfonyl Fluorides as possible therapeutic agents in Alzheimer's Disease: Structure/activity relationships as CNS selective cholinesterase inhibitors. In: Alzheimer's and Parkinson's Disease: Strategies in Research and Development, A. Fisher, C. Lachman and I. Hanin (Eds.), Plenum Press, New York, 1986, pp. 551–556.

Davies, P., and Maloney, A.J.R. Selective loss of central cholinergic neurons in Alzheimer's disease. Lancet, 2: 1403, 1976.

Perry, E.K., Tomlinson, B.E., Blessed, G., Bergman, K., Gibson, P.H., and Perry, R.H. Correlation of cholinergic abnormalities with senile plaques and mental test scores in senile dementia. Brit. Med. J.2; 1457–1459, 1978.

Whitehouse, P.J., Price, D.L., Struble, R.G., Clarke, A.W., Coyle, J.T., and DeLong, M.R. Alzheimer's disease and senile dementia: loss of neurons in the basal forebrain. Science2 15, 1237–1239, 1982.

Davies, P.: Theoretical treatment possibilities for dementia of the Alzheimer type: The cholinergic hypothesis. In: Strategies for the Development of an Effective Treatment of Senile Dementia, ed. by T. Crook and S. Gershon, Mark Powley Associates. New Canaan, CT, 1981, pp. 19–32.

Drachman, D.A., and Glosser, G.: Pharmacological strategies in aging and dementia: The cholinergic hypothesis. In: Strategies for the Development of an Effective Treatment of Senile Dementia, ed. by T. Crook and S. Gershon, Mark Powley Associates, New Canaan, CT, 1981, pp. 35–54.

Davis, K.L., and Mohs, R.C.: Enhancement of memory processes in Alzheimer's disease with multiple–dose intravenous physostigmine. Am. J. Psychia. 139, 1421–1424, 1982.

Thal, L.J., Fuld, P.A., Masur, D.M., and Sharpless, N.S.: Oral physostigmine and lecithin improve memory in Alzheimer disease. Ann. Neurol. 13, 491–496, 1983.

Giacobini, E. and Becker, R.: New cholinesterase inhibitors for treatment of Alzheimer's disease. In: Alzheimer's Disease Basic Mechanisms, Diagnosis and Therapeutic Strategies, ed. by K. Iqbal, D.R.C. McLachlan, B. Winblad and H.M. Wisniewski, John Wiley and Sons, New York, NY, 1991, pp. 627–631.

Deutsch, J.A.: The cholinergic synapse and the site of memory. Science 174, 788–794, 1971.

Reutter, S.A., Filbert, M.G., Moore, D.H., and Adler, M.: A role for butyrylcholinesterase in respiratory pathophysiology following nerve agent intoxication. In: Proceedings of the Sixth Medical Chemical Defense Biosciences Review, U.S. Army Medical Research and Development Command, U.S. Army Medical Institute of Chemical Defense, Aberdeen Proving Ground, Maryland, 1987, pp. 393–396.

Gauthier, S., Masson, H., Gauthier, L., Bouchard, R., Collier, B., Bacher, Y., Bailey, R., Becker, R., Bergman, H., Charbonneau R., Dastoor, D., Gayton, D., Kennedy, J., Kissel, C., Krieger, M., Kushnir, S., Lamontagne, A., St–Martin, M., Morin, J., Nair, N.P.V., Neirinck, L., Ratner, J., Suissa, S., Tesfaye, Y., and Vida, S. Tetrahydroaminoacridine and lecithin in Alzheimer disease. In: Current Research in Alzheimer Therapy; E. Giocobini and R. Becker, (Eds.), New York, Taylor and Francis, 1988. pp 237–245.

Moss, D.E., Rodriguez, L.A., Selim, S., Ellett, S.O., Devine, J.V., and Steger, R.: The sulfonyl fluorides: CNS–selective cholinesterase inhibitors with potential value in Alzheimer's disease? Neurology & Neurobiology vol. 18, Alan R. Liss, Inc., New York City, 1985, pp. 337–350.

(List continued on next page.)

Primary Examiner—Theodore J. Criares

(57) ABSTRACT

The present invention provides a pharmaceutical composition, comprising a sulfonyl fluoride and a pharmaceutically acceptable carrier. Also provided is a method of treating Alzheimer's disease in an individual in need of such treatment, comprising the step of administering to said individual a therapeutically effective dose of methanesulfonyl fluoride. Further provided is a method of enhancing cognitive performance in an individual in need of such treatment, comprising the step of administering to said individual a therapeutically effective dose of methanesulfonyl fluoride.

OTHER PUBLICATIONS

Pacheco, G., Palacios–Esquivel, R., and Moss, D.E. Cholinesterase inhibitors proposed for treating dementia in Alzheimer's disease: selectivity toward human brain acetylcholinesterase compared to butyrylcholinesterase. J. Pharmacol. Exper. Ther. 274, 767–770, 1995.

Mohs, R.C., Davis, B.M., Johns, C.A., Mathé, A.A., Greenwald, B.S., Horvath, T.B., and Davis, K.L. Oral physostigmine treatment of patients with Alzheimer's disease. Am. J. Psychiatry 142, 28–33, 1985.

Becker, R.E., Colliver, J., Elble, R., Feldman, E., Giocobini, E., Kumar, V., Markwell, S., Moriearty, P., Parks, R., Shillcutt, S.D., Unni, L., Vicari, S., Womack, C., and Zec, R.F. Effects of metrifonate, a long–acting cholinesterase inhibitor, in Alzheimer Disease: Report of an open trial. Drug Devel. Res. 19, 425–434, 1990.

Malin, D.H., Toups, P.J., Osgood, L.D., Fowler, D.E., Hunter, C.L., Arcangeli, K.R., and Moss, D.E.: Methanesulfonyl fluoride enhances one–trial learning in mid–aged rats. Neurobiol. Aging 12, 181–183, 1991.

Malin, D.H., Plotner, R.E., Radulescu, S.J., Perebee, R.N., Lake, J.R., Negrete, P.G., Schaefer, P.J., Crothers, M.K., and Moss, D.E.: Chronic methanesulfonyl fluoride enhances one–trial per day reward learning in aged rats. Neurobiol. Aging 14, 393–395, 1993.

Palacios–Esquivel, R.L., Pacheco, G., and Moss, D.E.: Methanesulfonyl fluoride (MSF) blocks scopolamine–induced amnesia in rats. Neurobiol. Aging 14, 93–96, 1993.

Grob, D., Lilienthal, J.L., Jr., Harvey, A.M., and Jones, B.F. The administration of di–isopropyl fluorophosphate (DFP) to man. Johns Hopkins Hospital Bulletin 81: 217–244, 1947.

Schwarz, R.D., Davis, R.E., Gracon, S., Hoover, T., Moos, W.H., and Pavia, M.R. Next generation tacrine. Neurobiology of Aging 12: 185–187, 1991.

Adem, A. The next generation of cholinesterase inhibitors. Acta Neurol Scand (Supplement) 149: 10–12, 1993.

Davidson, M., Hollander, F., Zemishlany, Z, Cohen L.J., Mohs, R.C. and Davis, K.L. Cholinergic agonists in Alzheimer's disease patients. In: Current Research in Alzheimer Therapy; E. Giacobini and R. Becker, (Eds.), Taylor and Francis, New York, 1988. pp 333–336.

Wiseman, E.J. and Jarvik, L.F. Potassium channel blockers: could they work in Alzheimer's disease? Alzheimer'S Disease and Associated Disorders 5(1): 25–30, 1991.

Waser, P.G., Berger, S., Haas, H.L., and Hofman, A. 4–Aminopuridine (4–AP)–derivatives as central cholinergic agents. In Current Research in Alzheimer Therapy, E. Giacobini and R. Becker, (Eds.), Taylor and Francis, New York, 1988. pp 337–342.

Wurtman, R.J., Blusztain, J.K., Growdon, J.H., and Ulus, I.H. Cholinesterase inhibitors increase the brain's need for free choline. In: Current Research in Alzheimer Therapy; E. Giacobini and R. Becker, (Eds.), Taylor and Francis, New York, 1988. pp 95–100.

Leber, P., Observations and suggestions on antidementia drug development, Alzheimer's Disease and Associated Disorders 10 (Supp 1): 31–35, 1966.

Drago et al., Effects of Cytidine–Diphosphocoline on Acetylcholine–Mediated Behaviors in the Rat, Brain Research Bulletin, 31: 485–89, 1993.

Etienne et al., Alzheimer disease: Lack of lecithin treatment for 3 months, Neurology 31: 1552–4, 1981.

Foster et al., An Enriched–Population Double–Blind, Placebo–Controlled, Crossover Study of Tacrine and Lecithin in Alzheimer's Disease, Dementia 7: 260–6, 1996.

Wettstein A., No Effect from Double–Blind Trial Physostigmine and Lecithin in Alzheimer Disease, Annals of Neurology 13:210–2, 1983).

Minthon et al., Oral Tetrahydroaminoacridine Treatment of Alzheimr's Disease Evaluated Clinically and by Regional cerebral Blook Flow and EEG, Dementia 4:32–42, 1993.

Yamazaki et al., FR121196, a Potential Antidementia Drug, Ameliorates the Impaired Memory of Rat in the Morris Water Maze, Journal of Pharmacology & Experimental Therapeutics 272: 256–63, 1995.

Matsuoka et al., Possible involvement of Brain somatostatin in the memory formation of rats and the cognitive enhancing action of FR121196 in passive avoidance task, Brain Research 642:11–19, 1994.

Delwaide et al., Acute effect of drugs upon memory of patients with senile dementia, Acta Psychiatrica Belg. 80:748–54, 1980.

Wesnes et al., Cholinesterase Inhibition inthe Scopolamine Model of Dementia, Annals of the New York Academy of Sciences 640:268–271, 1991 (HP–029.

Shutske et al.,9–Amino–1,2,3,4–tetrahydroacridin–1–ols: Synthesis and Evaluation as Potential Alzheimer's Disease Therapeutics, Journal of Medicinal Chemistry 32: 1805–1813, 1989.

Ashford et al., Physotigmine and Its Effects on Six Patients with Dementia, American Journal of Psychiatry 138: 829–30, 1981.

Cutler et al., Clinical safety, tolerance, and plasma level of the oral anticholinesterase 1,2,3,4–tetrahydro–9–aminoacridin–1–oL–maleate (HP–029) in Alzheimer's disease: preliminary findings. Journal of clinical pharmacology 30:556–61, 1990.

Zemlan et al., Double–Blind Placebo–Controlled Study of Velnachrine in Alzheimer's Disease, Life Sciences 58:1823–32, 1996.

Siegfried K. Human Psychopharmacology, The Efficay ofCholinergic Drugs in Patients with Alzheimer's Disease, 10:89–96, 1995.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–13 is confirmed.

* * * * *